United States Patent [19]
Ford

[11] Patent Number: 5,954,505
[45] Date of Patent: Sep. 21, 1999

[54] FORCE DISTRIBUTING DENTAL IMPLANT

[76] Inventor: Christopher W. Ford, 86 Labbe La., Leonard, Mich. 48367-2950

[21] Appl. No.: 09/035,521

[22] Filed: Mar. 5, 1998

[51] Int. Cl.⁶ .................................................. A61C 8/00
[52] U.S. Cl. ............................................ 433/177; 433/173
[58] Field of Search .................................. 433/169, 172, 433/173, 174, 175, 176, 177

[56] References Cited

U.S. PATENT DOCUMENTS

| | | |
|---|---|---|
| 2,688,799 | 9/1954 | Fluchiger et al. ..................... 433/177 |
| 3,380,161 | 4/1968 | Weissman ............................. 433/177 |
| 4,259,072 | 3/1981 | Hirabayashi et al. . |
| 4,568,285 | 2/1986 | Chiaramonte et al. . |
| 4,609,354 | 9/1986 | Koch . |
| 4,657,510 | 4/1987 | Gittleman . |
| 4,938,693 | 7/1990 | Bulakiev . |
| 5,040,982 | 8/1991 | Stefan-Dogar . |
| 5,362,235 | 11/1994 | Daftary . |
| 5,425,639 | 6/1995 | Anders . |
| 5,453,007 | 9/1995 | Wagher . |
| 5,468,150 | 11/1995 | Brammann . |
| 5,503,558 | 4/1996 | Clokie . |
| 5,752,830 | 5/1998 | Suarez .................................... 433/173 |

OTHER PUBLICATIONS

"Clinical And Statistical Analysis Of A Comprehensive Implant Reconstructive Practice", Richard A. Borgner, DDS, *Dental Economics*, Oct. 1995, p. 96.
"Survival Rates of Hemisected Teeth: An Attempt to Compare them with Survival Rates of Alloplastic Implants", Buhler, Hans. *Edodontics Peridontics Review*, Fall 1996.
"Early Bone Loss Etiology And its Effect on Treatment Planning", Carl E. Misch, DDS, MDS, *Dentistry Today*, Jun. 1996, pp. 44–51.
"From Subperiosteal to Osseointegration: An Unusual Demand Met by an Unusual Approach", Gary H. Ganz, DDS, PC, *Dentistry Today*, Oct. 1995, pp. 49–51.
"Controlling Forces on Dental Implants", Dr. Paul Homoly, *Dentistry Today*, Oct. 1995, pp. 46–47.
"Osseointegrated Implants With an Intramobile Element in the Treatment of Edentulous Jaws", Alan F. Shernoff, DDS, et al., *Compend Contin Educ. Dent.*, vol. XII, No. 6, pp. 394–402.
"Implant–Protected Occlusion", Carl E. Misch, DDS, MDS and Martha W. Bidez, PhD. *PP&A*, vol. 7, No. 5, pp. 25–29.
"Interrelations of Soft and Hard Tissues for Osseointegrated Implants" by Oded Bahat, BDS, MSD, *Compendium*, Dec. 1986, vol. 17, No. 12, pp. 1161–1167.
"Diagnosis and Evaluation of Complications and Failures Associated With Osseointegrated Implants", Harold S. Baumgarten, DMD and Gerald J. Chiche, DDS, *Compendium*, Aug. 1995, vol. 16, No. 8, pp. 814–823.
"Techniques for Ideal Implant Placement in the Mandibular First Molar Position", Louis F. Clarizio, DDS, *Compendium*, Aug. 1995, vol. 16, No. 8, pp. 806–813.
"Implant–Protected Occulsion: A Biomedical Rationale", Carl F. Misch, DDS, MDS and Martha Warren Bidez, PhD, *Compendium*, Nov. 1994, vol. 15, No. 11, pp. 1330–1343.

*Primary Examiner*—Nicholas D. Lucchesi
*Attorney, Agent, or Firm*—Harness, Dickey & Pierce, P.L.C.

[57] ABSTRACT

The preferred embodiment consists primarily of an anchor for implantation into the patient's crestal bone or other suitable bony structure, an insert which is flexibly received within the anchor and would be mounted so as to allow modulation of forces being transferred from the insert to the anchor. The insert would also act as a platform for mounting the prosthetic or artificial tooth. The prosthesis allows elastic movement of the artificial tooth along three orthogonal axes.

15 Claims, 3 Drawing Sheets

FORCE DISTRIBUTING DENTAL IMPLANT

BACKGROUND OF THE INVENTION

Dental implants of numerous and varying design have been around for many years. These implants seek to restore natural dental function. The human tooth and its attachment to the jaw, however, is a complex system, not easily capable of replication. Prior art implants were generally directly attached to the bone. The implant itself would be made of metal and/or ceramic. The prior art implants essentially did not move along any axes.

An implant can become overloaded during the patient's use and it will become loose through bone loss or in more extreme cases, break. Even upon removal of the forces, the implant remains loose and is usually eventually lost.

In an effort to produce long lasting implants, reduce breakage and prosthetic failure, the prior art contains examples of multiple implants, varying orientation of implants, varying diameter and lengths of implants, implant protected occlusion, varying surface areas, occlusal table width, varying loading schedules, varying implant locations, splinting, patient selection, soft tissue considerations, etc. See, for example: U.S. Pat. Nos. 5,453,007 to Wagher; 5,040,982 to Stefan-Dogar; 5,468,150 to Brammann; 4,657,510 to Gittleman; 5,503,558 to Clokie; 4,259,072 to Hirabayashi et al.; 4,568,285 to Chiaramonte et al.; 4,938,693 to Bulakiev; 4,609,354 to Koch; 5,425,639 to Anders; 5,362,235 to Daftary; "*Clinical And Statistical Analysis Of A Comprehensive Implant Reconstructive Practice*: by Richard A. Borgner, DDS *Dental Economics*, October 1995, p. 96; "*Survival Rates of Hemisected Teeth: An Attempt to Compare them with Survival Rates of Alloplastic Implants*" by Buhler, Hans, *Endodontics/Peridontics Review*, Fall 1996; "*Early Bone Loss Etiology And its Effect on Treatment Planning*" by Carl E. Misch, DDS, MDS, *Dentistry Today*, June 1996, pp. 44–51; "*From Subperiosteal to Osseointegration: An Unusual Demand Met by an Unusual Approach*" by Gary H. Ganz, DDS, PC, *Dentistry Today*, October 1995, pp.49–51; "*Controlling Forces on Dental Implants*" by Dr. Paul Homoly, *Dentistry Today*, October 1995, pp. 46–47; "*Osseointegrated Implants With an Intramobile Element in the Treatment of Edentulous Jaws*" by Alan F. Shernoff, DDS et al., *Compend Contin Educ Dent*, Vol. XII, No. 6, pp. 394–402; *Implant-Protected Occlusion*" by Carl E. Misch, DDS, MDS and Martha W. Bidez, PhD, *PP&A*, Vol. 7, No. 5, pp. 25–29; "*Interrelations of Soft and Hard Tissues for Osseointegrated Implants*" by Oded Bahat, BDS, MSD, *Compendium*, December 1996, Vol. 17, No. 12 pp. 1161–1167; "*Diagnosis and Evaluation of Complications and Failures Associated With Osseointegrated Implants*" by Harold S. Baumgarten, DMD and Gerald J. Chiche, DDS, *Compendium*, August 1995, Vol. 16, No. 8, pp. 814–823; "*Techniques for Ideal Implant Placement in the Mandibular First Molar Position*" by Louis F. Clarizio, DDS, *Compendium*, August 1995, Vol. 16, No. 8, pp. 806–813; and "*Implant-Protected Occlusion: A Biomechanical Rationale*" by Carl F. Misch, DDS, MDS and Martha Warren Bidez, PhD, *Compendium*, November 1994, Vol. 15, No. 11, pp. 1330–1343. Many of these considerations and considerable failure of prior art prostheses is due to a lack of replicating the ability of a natural tooth to move along three axes.

The prior art has therefore resulted in implants that are often directly attached to the bone and that cannot flex with the bone. Loads are, therefore, concentrated at the crestal bone. This concentration of stress on the bone results in the physiological phenomenon known as resorption. The density and mass of the crestal bone decreases, eroding support for the implant. The final result is loss of the implant due to lack of support.

THE PRESENT INVENTION

A natural tooth moves along three axes. In natural dentition, a ligament or fibrous tissue connects the tooth to the bone and acts as a shock absorber for the force being transferred from the tooth to the crestal bone. Thus, the force applied on the tooth from chewing, etc. is absorbed by the bone over a longer period of time and distributed throughout the attachment of the tooth to the bone. This latter function is aided by the shape of the root which allows the force to be distributed over the entire length of the root. The transfer of force from tooth to bone is also aided by an approximately equal modulus of elasticity in both tooth and bone. In natural dentition, a load upon the tooth will be transmitted in part by allowing movement of the tooth relative to the bone. In an overload situation, the ligament space will increase allowing more movement of the tooth which lowers the forces to the surrounding bone. When the overload situation is removed, the tooth will return to its normal rigidity.

The present invention seeks to allow the dental implant to move and respond to forces in a manner similar to the natural tooth thereby greatly reducing or eliminating the possibility of bone resorption, implant failure and/or loss of the prosthesis.

A further object of the invention is to allow an implant to be rigidly mounted into the patient's crestal bone, yet still have the implant accommodate forces transmitted from normal use of the prosthesis.

Another object of the invention is to provide a dental implant that would expose the patient to only biocompatible materials in a system that replicated the modulus of elasticity of the natural tooth and bone system.

DETAILED DESCRIPTION OF THE PREFERRED EMBODIMENT

The preferred embodiment consists primarily of an anchor for implantation into the patient's crestal bone or other suitable bony structure, an insert which is flexibly received within the anchor and would be mounted so as to allow modulation of forces being transferred from the insert to the anchor. The insert would also act as a platform for mounting the prosthetic or artificial tooth.

Figure 1:
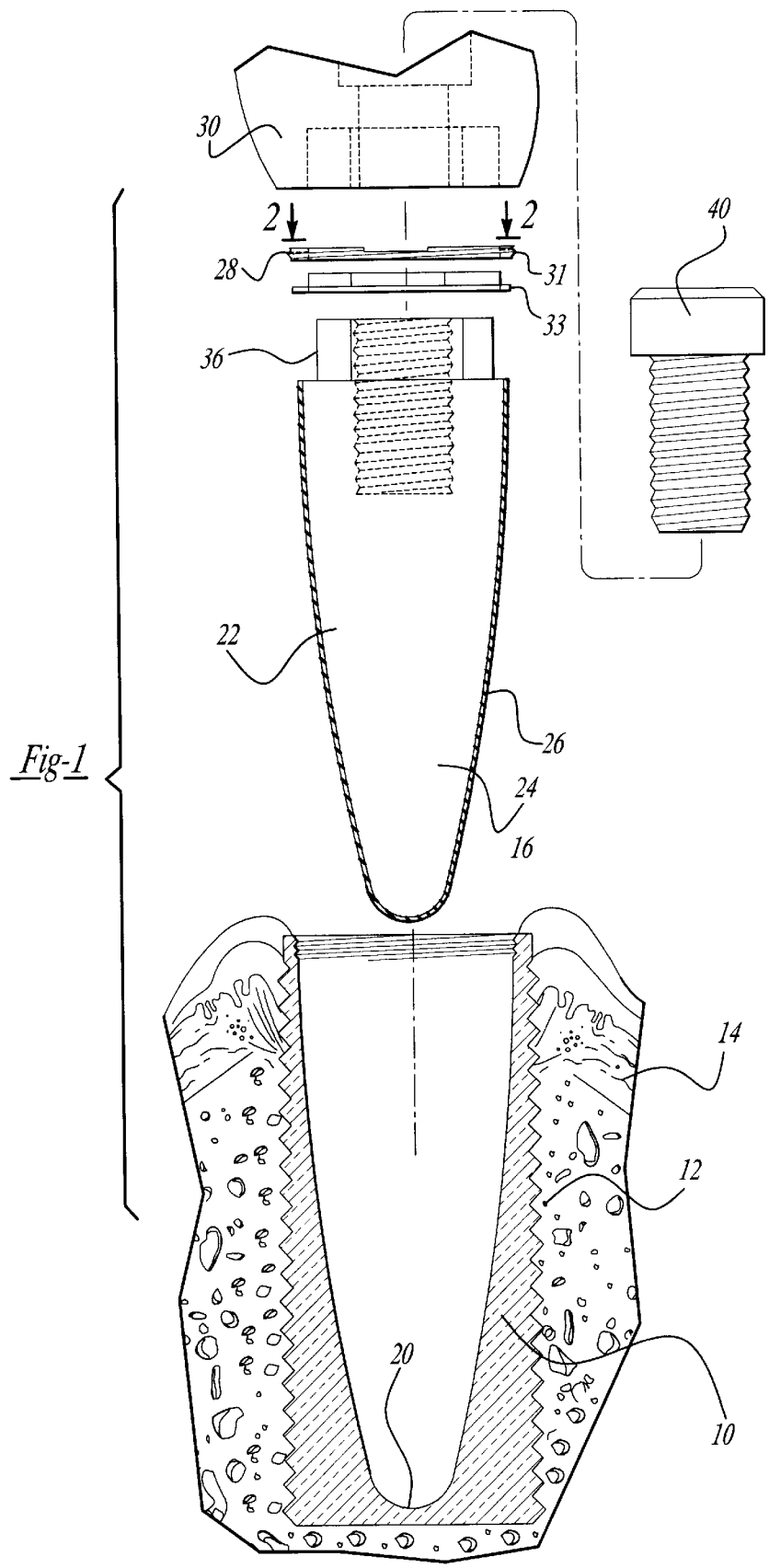
FIG. 1 is an exploded partial section side view of the present invention.
Figure 2:
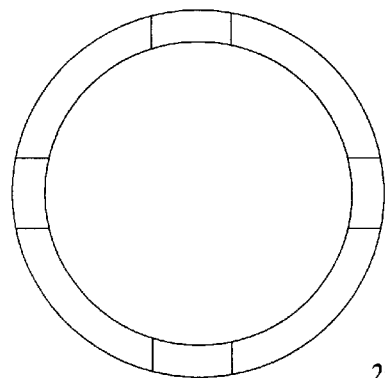
FIG. 2 is a plan view of a retaining ring.

As shown in FIG. 1, the anchor 10 is preferably a titanium alloy which is biocompatible, although other biocompatible metal alloys could be used, such as cobalt chromium alloys. The anchor could also be coated with hydroxyapatite (HA) 12 or other bone ingrowth stimulants. The anchor is designed to be inserted into the crestal bone 14 of the patient through ordinary means, such as the surgical drilling of a hole and subsequent placement of the anchor. The anchor can be threaded, smooth, or vented on its attachment surface for this type of attachment by known means.

Figure 4:
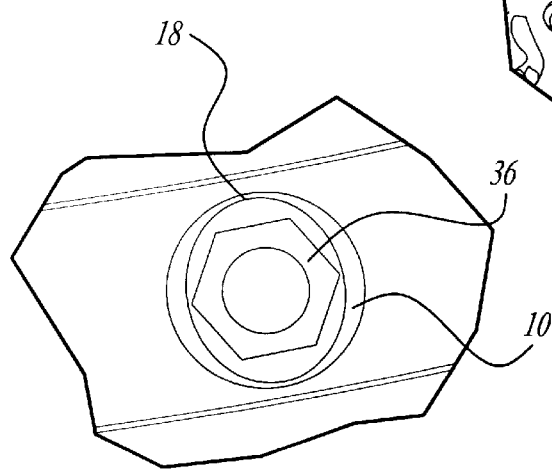
FIG. 4 is a plan view of the invention implanted in the jaw.
Figure 5:
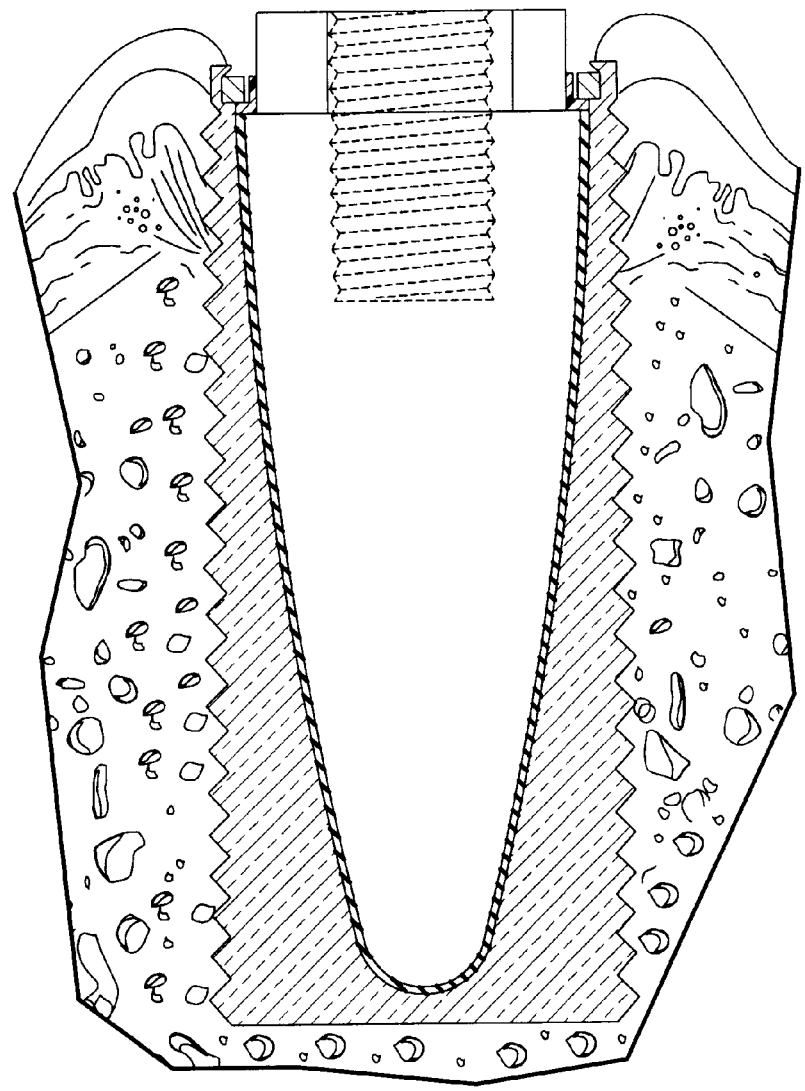
FIG. 5 is a partial cross section of a portion of the invention implanted.

Internally, the anchor has an interior wall 16 defining a pocket. In a horizontal plane (buccal-lingual orientation) the pocket is preferably somewhat ovoid 18. (FIG. 4) Along an inciso-cervical axis the pocket preferably tapers distally to a rounded end 20.

Figure 3:
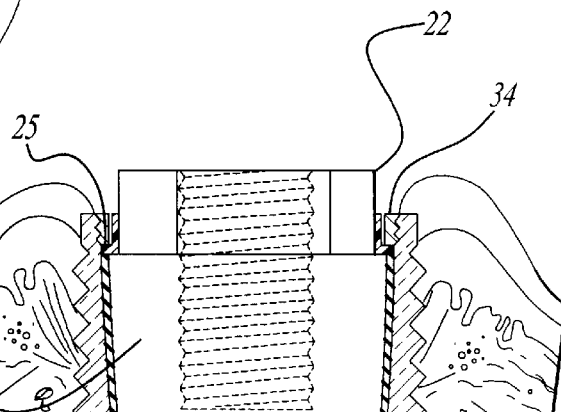
FIG. 3 is a partial cross section of a portion of the invention implanted.

Turning to FIG. 3, an insert 22 is sized to fit within the pocket of the anchor. The insert is designed to have elastic properties to replicate the function of the original ligament or fibrous tissues holding the natural tooth and allowing movement of the prosthesis in response to various loads placed upon the prosthesis in the three orthogonal axes. These axes are the apical or vertical axis, the facio-lingual axis, and the mesio-distal axis. The insert is preferably made of two materials, a core 24 and a layer of resilient material 26. The core is relatively rigid, such as one made of titanium alloy. The insert is designed to fit within and substantially fill the pocket of the anchor and to move in response to occlusal forces. The insert is tapered to fit within the pocket and along the apical axis to more evenly distribute varying levels of occlusal forces.

The resilient material is selected and the layer sized to replicate natural tooth movement. According to Parfitt, Parfift GS Measurement of the physiologic mobility of individual teeth in an axial direction, J Dent Res 1960; 39:68, a natural tooth may move in an apical direction 28 microns with an axial load. A natural tooth moves 56 to 108 microns in response to lateral forces with a movement of 56–75 microns buccal-lingually. A natural tooth also has the phenomenon of pivoting and pivots about a point two thirds towards the apex. By resilient material, it is meant material that has elastic properties. The resilient material should be selected to have a modulus of elasticity that, in combination with the rest of the implant system, allows an overall modulus of elasticity similar to that found in a normal tooth-ligament combination. The resilient material can be of various plastics, such as nylon, Delrin, high molecular weight polyethylene or the equivalent.

The insert should be retained by a fixation means 28, such as a screw ring 31 or snap ring retainer 25 (FIG. 3) operating in conjunction with the anchor. These fixation means allow the insert to be retained in the anchor against normal loads produced during patient use. A snap ring provides a collapsible collar on the insert which when installed also fits within a groove 34 about the inner circumference of the anchor. The collar is collapsed to reduce its diameter to fit within the groove. When the collapsing force is removed, the collar resumes its unbiased diameter which resists removal through interference fit. A threaded fixation means 30 (see FIG. 1) allows a collar to be screwed onto the anchor and hold down the insert by covering the shoulder of the insert. A washer 33 may be added. These fixation mechanisms allow for retrieval of the insert for adjustment, modification, replacement, etc. The superior portion of the insert extending beyond the anchor and fixation device can be fitted with a cap retaining feature, such as a hex stud 36 to receive the prosthetic cap or dentin replacing portion 30 of the prosthesis. The dentin replacing portion of the prosthesis can be affixed through known techniques such as either being cemented in place or retained by a set screw 40 placed longitudinally into the hex portion 36. The prosthetic cap can be made of conventional dental materials, such as ceramics, metals and/or resins. The materials from which the prosthetic cap is constructed should be considered from the viewpoint of their modulus of elasticity and their contribution to the modulus of elasticity of the prosthesis as a whole. For example, the modulus elasticity of titanium is approximately five times more than cortical bone. Likewise, cobalt chromium and stainless steel used for implants is in the range of twice the modulus of elasticity of that of titanium, with the modulus of elasticity of ceramics being even higher. See, e.g. Misch, Early Bone Loss Etiology and Its Effect on Treatment Planning, Dentistry Today June 1996, p. 43.

In use, the prosthesis would involve screening the patient for proper amount of crestal bone, as well as other morbidity factors. Once the proper occlusal scheme was selected, the patient would be prepared for surgical insertion of the anchor. The insert would be selected to work in combination with the anchor and the selected prosthetic cap to give a range of motion of the implant along the various axes to replicate the range of motion of a natural tooth in a "normal" patient as discussed above, or to replicate the movement of natural teeth in the particular patient. The crestal bone 14 would be exposed, drilled and tapped. The anchor 10 would be threaded in. The insert 22 would be inserted into the anchor 10. The insert would be retained with retaining means 28, which would be screwed down with a tool such as a ratchet in the case of a threaded retainer or a pair of snap ring pliers for one of the alternate embodiments. The prosthetic cap 30 would be placed over the anchor-insert combination to encapsulate the insert. The cap could be secured by a set screw 40 rotated by an alien wrench. This encapsulation preferably results in an integral single chamber which would not allow for the ingress or egress of materials to or from the chamber, such as saliva, food particles, implant particles, etc. Thus, while the prosthetic device is made entirely out of biocompatible materials, encapsulation of the insert allows for a greater range of. possible materials to be selected without raising biocompatibility issues. This allows a more precise tailoring of the modulus elasticity of the overall prosthesis to replicate that of the natural tooth and ligament.

What is claimed is:

1. A prosthesis for restoring functional dentition comprising:
    an anchor for rigid attachment to a patient's crestal bone, said anchor including a pocket; and
    an elastic insert receivable within said anchor pocket for modulating the transmission of force from a cap to the anchor, said insert having a complementary shape to said pocket to substantially fill said pocket, a discrete and separate fixation member for retaining said insert in said anchor and wherein said cap is securable to said anchor and encases said insert from bodily fluids of said patient.

2. The prosthesis of claim 1 which has a modulus of elasticity on the order of that of a natural tooth and ligament combination.

3. The prosthesis of claim 1 where once installed allows elastic motion of said cap at least 56–75 microns buccal-lingually.

4. The prosthesis of claim 3 wherein the cap can move elastically along an inciso cervical axis.

5. The dental prosthesis of claim 3 wherein said insert further comprises a biologically inert core that substantially fills said anchor and a resilient material bonded to the surface of said core that substantially fills the remainder of the space within said anchor.

6. The prosthesis of claim 5 wherein said resilient material further comprises nylon.

7. The prosthesis of claim 1 where once installed allows elastic movement of said cap along inciso-cervical, mesial-distal and buccal-lingual axes.

8. The prosthesis of claim 1 wherein said cap is releasably secured to said anchor.

9. A dental prosthesis comprising:
- a cap which provides an occlusal bearing surface for patient use;
- an anchor for rigid attachment to said patient's bone which, when attached to said cap, defines a single chamber sealed from outward migration of biologically non-inert substances;
- an insert further comprising a rigid piece with attached elastic material for substantially filling said chamber; and
- a discrete and separate fixation member for retaining said insert in said anchor.

10. The prosthesis of claim 9 wherein said insert allows modulation of forces along three orthogonal axes.

11. A dental prosthesis for modulating forces transmitted from a dentin replacing surface to the crestal bone comprising:
- an anchor for rigid attachment to said crestal bone, said anchor including a pocket;
- a dentin replacing cap for releasable securement to said anchor; and
- an insert to be interpsed between said anchor and said cap, said insert having a complementary shape to said pocket to substantially fill said pocket, a discrete and separate fixation member for retaining said insert in said anchor and said insert further comprising a resilient member for allowing the dentin replacing cap to move at least 50 microns buccal-lingually.

12. The prosthesis of claim 11 wherein said insert is interposed in a biologically shielded environment.

13. The prosthesis of claim 11 wherein said resilient member further comprises a rigid structure at least partially coated with a resilient coating to the extent necessary to achieve a modulus of elasticity of said prosthesis on the order of the patient's natural modulus for the tooth and ligament combination.

14. The prosthesis of claim 11 wherein said dentin replacing cap can move along three orthogonal axes in response to occlusal forces.

15. A method for implanting a dental prosthesis comprising rigidly attaching an anchor to the patient's crestal bone;
- placing an insert in said anchor, said insert further comprising an elastic member for modulating forces transmitted to said anchor, releasably capping said insert so as to biologically shield said insert from said patient.

* * * * *